United States Patent
Bar

(10) Patent No.: US 11,202,647 B2
(45) Date of Patent: Dec. 21, 2021

(54) APPARATUS AND A METHOD FOR CLOT AND PLAQUE RETRACTING

(71) Applicant: INRETIO LTD., Bitzaron (IL)

(72) Inventor: Eli Bar, Megadim (IL)

(73) Assignee: INRETIO LTD, Bitzaron (IL)

( * ) Notice: Subject to any disclaimer, the term of this patent is extended or adjusted under 35 U.S.C. 154(b) by 180 days.

(21) Appl. No.: 16/479,990

(22) PCT Filed: Jan. 23, 2018

(86) PCT No.: PCT/IB2018/050407
§ 371 (c)(1),
(2) Date: Jul. 23, 2019

(87) PCT Pub. No.: WO2018/134801
PCT Pub. Date: Jul. 26, 2018

(65) Prior Publication Data
US 2019/0365397 A1 Dec. 5, 2019

Related U.S. Application Data

(60) Provisional application No. 62/449,296, filed on Jan. 23, 2017.

(51) Int. Cl.
*A61B 17/221* (2006.01)
*A61B 17/00* (2006.01)
*A61B 17/22* (2006.01)

(52) U.S. Cl.
CPC .. *A61B 17/221* (2013.01); *A61B 2017/00867* (2013.01); *A61B 2017/00893* (2013.01); *A61B 2017/2215* (2013.01); *A61B 2017/22038* (2013.01); *A61B 2017/22069* (2013.01); *A61B 2017/22082* (2013.01)

(58) Field of Classification Search
CPC ........ A61B 17/221; A61B 2017/00867; A61B 2017/00893; A61B 2017/22038; A61B 2017/22069; A61B 2017/22082; A61B 2017/22094; A61B 2017/2212; A61B 2017/2215; A61B 2017/320716; A61F 2/013; A61F 2002/016; A61F 2230/0069; A61F 2230/0093
See application file for complete search history.

(56) References Cited

U.S. PATENT DOCUMENTS

| | | | |
|---|---|---|---|
| 8,382,771 B2 | 2/2013 | Gellman et al. | |
| 8,444,661 B2 | 5/2013 | Nair et al. | |
| 8,852,205 B2 | 10/2014 | Kipke et al. | |

(Continued)

FOREIGN PATENT DOCUMENTS

WO 2011/119872 A1 9/2011

*Primary Examiner* — Jocelin C Tanner
(74) *Attorney, Agent, or Firm* — Browdy and Neimark, PLLC

(57) ABSTRACT

An apparatus, device and method are provided for executing a clot or plaque removal procedure. In one embodiment, a clot removal device may include a clot holding element for penetrating a target clot and stabilizing the clot in its position; a controllable distal filter that can be extended to cover the target clot; a distal filter, openable downstream from the clot, designed to substantially prevent flow through of clot elements, and further designed to drag the clot out of a vessel, for retrieving by the clot removal device.

17 Claims, 11 Drawing Sheets

(56) References Cited

U.S. PATENT DOCUMENTS

| | | | |
|---|---|---|---|
| 2005/0085826 A1* | 4/2005 | Nair | A61B 17/221 606/113 |
| 2007/0088383 A1 | 4/2007 | Magnuson | |
| 2007/0249998 A1 | 10/2007 | Ngo | |
| 2010/0268265 A1* | 10/2010 | Krolik | A61B 17/221 606/200 |
| 2011/0152920 A1 | 6/2011 | Eckhouse | |
| 2011/0202088 A1 | 8/2011 | Eckhouse | |
| 2012/0059356 A1 | 3/2012 | Di Palma et al. | |
| 2013/0345739 A1* | 12/2013 | Brady | A61B 17/221 606/200 |
| 2014/0100597 A1* | 4/2014 | Wang | A61F 2/012 606/200 |
| 2014/0121672 A1* | 5/2014 | Folk | A61B 17/221 606/127 |
| 2014/0128905 A1* | 5/2014 | Molaei | A61B 17/221 606/200 |
| 2014/0276922 A1* | 9/2014 | McLain | A61B 17/221 606/128 |
| 2014/0303667 A1 | 10/2014 | Cox et al. | |
| 2015/0250497 A1* | 9/2015 | Marks | A61B 17/221 606/159 |
| 2015/0265299 A1 | 9/2015 | Cooper et al. | |

* cited by examiner

APPARATUS AND A METHOD FOR CLOT AND PLAQUE RETRACTING

CROSS REFERENCE TO RELATED APPLICATIONS

This application claims priority from U.S. Provisional Patent Application No. 62/449,296, filed 23 Jan. 2017, entitled "Clot and plaque retractor via extendable distal or proximal filter mesh", which is incorporated in its entirety herein by reference.

FIELD OF THE INVENTION

The present invention relates to methods and devices useful in clot removing procedures.

BACKGROUND OF THE INVENTION

Strokes are the third leading cause of death in US and worldwide, following heart disease and cancer. They kill more than 160,000 people each year in the US, and is the leading cause of adult disability. Ischemic strokes occur when a blood vessel carrying blood to the brain is blocked by a blood clot. This causes blood not to reach the brain, or part of the brain. Ischemic strokes account for about 87% of all strokes. An ischemic stroke can occur in two ways—Cerebral thrombosis (a blood clot or plaque blocks an artery that supplies a vital brain center), and Cerebral embolism (a blood clot breaks off from a thrombus elsewhere in the body, lodges in a blood vessel in the brain and shuts off blood supply to that part of the brain). High blood pressure is the most important risk factor for this type of stroke.

One of the primary treatments for strokes are urgent clot removal procedures, however there are significant challenges associated with designing clot removal devices that can deliver high levels of protection.

There are numerous access challenges that make it difficult to appropriately deliver clot removal devices. In cases where access involves navigating the aortic arch (such as coronary or cerebral blockages), the configuration of the arch in some patients makes it difficult to position a guide catheter. These difficult arch configurations are classified as either type 2 or type 3 aortic arches, where type 3 arches present the most difficulty.

In addition, the tortuosity challenge is even more severe in the arteries approaching the brain. For example, it is not unusual at the distal end of the internal carotid artery that the device will have to navigate a vessel segment with a 180° bend, a 90° bend, and a 360° bend in quick succession over a few centimeters of vessel. In the case of pulmonary embolisms, access may be gained through the venous system and then through the right atrium and ventricle of the heart. The right ventricular outflow tract and pulmonary arteries are delicate vessels that can easily be damaged by inflexible or high-profile devices. For these reasons it is desirable that the clot retrieval device be compatible with as low profile and flexible access, and that such devices can support catheters as possible.

The vasculature in the area in which the clot may be lodged is often fragile and delicate. For example, neurovascular vessels are more fragile than similarly sized vessels in other parts of the body and are in a soft tissue bed. Excessive tensile forces applied on these vessels could result in perforations and hemorrhage. Pulmonary vessels are larger than those of the cerebral vasculature, but are also delicate in nature, particularly those more distal vessels.

Moreover, a clot may comprise any number of morphologies and consistencies. For example, long strands of softer clot material may tend to lodge at bifurcations or trifurcations, resulting in multiple vessels being simultaneously occluded over significant lengths. More mature and organized clot material is likely to be less compressible than softer fresher clot, and under the action of blood pressure it may distend the compliant vessel in which it is lodged. Furthermore, the inventors have discovered that the properties of the clot may be significantly changed by the action of the devices interacting with it. In particular, compression of blood clots may cause dehydration of the clot and may result in a dramatic increase in both clot stiffness and the coefficient of friction.

Clots may not only range in shape and consistency, but also may vary greatly in length, even in any one given area of the anatomy. For example, clots occluding the middle cerebral artery of an ischemic stroke patient may range from just a few millimeters to several centimeters in length.

Stent-like clot retrievers are being increasingly used to remove clot from cerebral vessels of acute stroke patients. These are self-expanding devices, similar in appearance to a stent attached to the end of a long shaft, and are advanced through a microcatheter and deployed across clot obstructions in order to trap and retrieve them. They typically rely on a pinning mechanism to grab the clot by trapping the clot between the self-expanding stent-like body and the vessel wall. This approach has numerous disadvantages, as follows.

A stent-like clot retriever relies on its outward radial force (RF) to retain its grip on the clot. If the RF is too low the stent-like clot retriever will lose its grip on the clot, but if the RF is too high the stent-like clot retriever may damage the vessel wall and may require too much force to withdraw. Therefore stent-like clot retrievers that have sufficient radial force to deal with all clot types may cause vessel trauma and serious patient injury, and stent-like clot retrievers that have appropriate radial force to remain atraumatic may not be able to effectively handle all clot types.

The stent-like clot retriever pinning mechanism tends to compress the trapped clot. This compressive force will tend to dehydrate the clot, which in turn tends to increase its coefficient of friction, making it more difficult to remove from the vessel.

Conventional Stent-like clot retriever designs do not retain their expanded shape very well when placed in tension in bends, due to the manner in which their strut elements are connected to one another. This can result in a loss of grip on a clot as the stent-like clot retriever is withdrawn proximally around a bend in a tortuous vessel, with the potential escape of the captured clot. This occurs because the struts of the stent-like clot retriever are placed in tension when it is retracted. This tension is due to friction between the device and the blood vessel, and is increased if an additional load is applied, such as that provided by a clot. In a bend, the struts on the outside of the bend are placed in higher tension than those on the inside. In order to attain the lowest possible energy state, the outside surface of the stent moves towards the inside surface of the bend, which reduces the tension in the struts, but also reduces the expanded diameter of the stent-like clot retriever.

Another disadvantage with this approach is that it relies on pinning the clot between the stent-like clot retriever and the vessel wall and thus may not restrain the clot effectively when passing a branch vessel or when passing into a vessel that is larger than the fully expanded diameter of the stent-like clot retriever.

Additionally, pinning the clot between the stent-like clot retriever and the vessel wall in order to remove it from the vessel also tends to cause high shear forces against the side of the clot as it is removed, potentially releasing fragments of the clot. If these fragments are not retained by the device, they may be released leading to further blockages in the distal vasculature. In addition, fragments can also be released during device retraction.

A particular difficulty encountered when attempting to remove long clots is that conventional devices may be shorter than the clot itself. A device that is shorter than the clot is unlikely to be able to restore flow through the occluded area upon deployment, and thus the pressure gradient across the clot remains a significant impediment to its removal. Since making such a device that can capture the long clot is essential, this would likely render it difficult to track through tortuous anatomies and could be traumatic to the vasculature, taking more force to withdraw and potentially getting stuck, and requiring surgery to remove.

For many reasons, including some or all of the above limitations, it is often necessary for a physician to make multiple passes with a clot retrieval device in order to fully remove an obstructive clot. However, each time a clot retrieval device is withdrawn the access to the target site is lost. Thus, it is necessary to re-advance a guidewire and microcatheter to access and re-cross the clot, and then remove the guidewire and advance the clot retrieval device through the microcatheter. Navigating the guidewire and microcatheter to the clot can take a considerable amount of time, especially if the vessels are tortuous. This additional time and device manipulation all adds to the risks to which the patient is exposed.

The challenges described above need to be overcome for any device to provide a high level of success in removing clot, restoring flow and facilitating good patient outcomes. Existing devices do not adequately address these challenges.

SUMMARY OF THE INVENTION

An apparatus, device and method are provided for executing a clot or plaque removal procedure. In one embodiment, a clot removal device may include a clot holding element for penetrating a target clot and stabilizing the clot in its position; a controllable distal filter that can be extended to cover the target clot; a distal filter, openable downstream from the clot, designed to substantially prevent flow through of clot elements, and further designed to drag the clot out of a vessel, for retrieving by the clot removal device.

In further embodiments, the clot removal device further comprises a proximal filter, designed to encapsulate the target clot prior to retrieval by the clot removal device.

In further embodiments, the distal filter and the proximal filter are designed to connect to each other to secure a captured clot within the clot removal device.

In further embodiments, the clot removal device further comprises a proximal balloon, designed to encapsulate the target clot prior to retrieval by the clot removal device.

In further embodiments, the clot holding element includes a memory material frame designed to expand inside the clot to stabilize the clot in its current position.

In further embodiments, the distal filter has gap sizes of a plurality of sizes, to enable substantial prevention of clot portion escape while enabling substantial blood flow during a clot removal procedure.

In further embodiments, the distal filter is designed to be openable when in a position downstream from the target clot.

In further embodiments, the clot removal device further comprises a treatment catheter designed to maintain the clot removal device elements crimped inside the catheter during insertion into a vessel, and enabling controlled expansion and/or contraction of one or more clot removal device elements during a clot removal procedure.

According to some embodiments, a method for clot removal from a vessel is provided, that includes advancing a treatment catheter carrying a clot removal device in a vessel towards a target clot to be removed; advancing the clot removal device to a position proximal to a target clot; extending a guide wire through the target clot; expanding a distal mesh on the distal side of the clot; expanding a clot stabilizing wire inside the clot; and withdrawing the distal mesh with the stabilized clot into the treatment catheter, for retrieval from the vessel.

In further embodiments, the method of clot removal includes expanding a proximal mesh on the proximal side of the clot; and withdrawing the distal mesh with the stabilized clot towards the proximal mesh, thereby securing the clot in a clot holding area, during retrieval from the vessel.

In further embodiments, the method of clot removal includes expanding a proximal balloon on the proximal side of the clot; and withdrawing the distal mesh with the stabilized clot towards the proximal balloon, thereby securing the clot in a clot holding area, during retrieval from the vessel.

In further embodiments, the method of clot removal includes applying one or more anticoagulant compounds.

In further embodiments, the method of clot removal includes applying one or more medication compounds.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

Figure 1A:
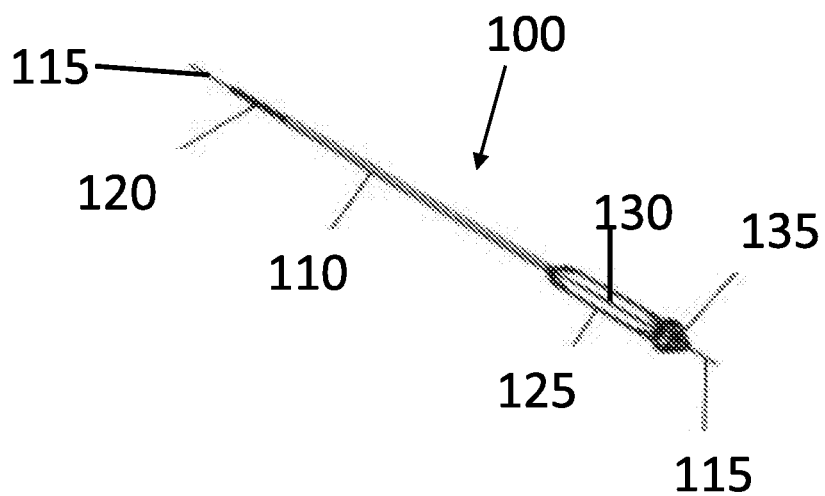
FIG. 1A is a schematic diagram of a clot removal device with distal filter, deployed position while it is mounted on a guide wire according to some embodiments.

It will be appreciated that for simplicity and clarity of illustration, elements shown in the drawings have not necessarily been drawn to scale. For example, the dimensions of some of the elements may be exaggerated relative to other elements for clarity. Further, where considered appropriate, reference numerals may be repeated among the drawings to indicate corresponding or analogous elements throughout the serial views.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention.

Non-limiting embodiments of the invention include a Protected/Securing Clot Retriever that secures the clot in its retraction phase, via an Adjustable Distal Filter, for example for Ischemic stroke cases.

Specifically, embodiments of the present invention include an apparatus and a method for clot and plaque retraction in the circularly blood system, while maintaining the blood flow.

The clot removal apparatus described herein contains a controllable distal filter and/or a proximal filter, for securing a clot being retrieved or extracted. This apparatus thereby prevents the clot or plague, or parts thereof, from being released downstream or upstream in the blood circulation system. In this apparatus, the filter may be a dynamic pocket that can become larger as necessary and fold up proximally (eg. the filter pocket may have a length of 5-150 mm, or less or more if needed.

The clot removal apparatus described herein may enable safe and dynamic capture and removal of a clot, and removal of the filter and clot via the apparatus, thereby preventing the escape of primary or and breakaway clot or plaque, and allowing for safe clot/plaque retrieving from the artery, and out of body.

In further embodiments, the clot removal apparatus described herein may include a clot holder device (e.g. TreVo-XP by Stryker) that may cut through the target clot and secure it in place, while the filter will wrap up over the clot or over the clot holder, and enable its safe removal.

According to some embodiments, the clot removal apparatus may specifically used to remove clots or plaque from the arteries in the brain (e.g. carotid artery and higher-level arteries). Of course, other arteries and/or veins may also be treated.

FIGS. 1A-1G are schematic diagrams of a clot removal device with a distal clot capture filter, according to some embodiments. As can be seen in FIG. 1A, clot removal device 100 may be mounted on a guide wire 115. Clot removal device 100 may be initially crimped in a guiding catheter 110. Upon deployment of clot removal device 100 into a target artery, positioned adjacent to a target clot, one or more elements may be deployed outside guiding catheter 110. Clot removal device 100 may be controlled with multiple control wires or strings, such as guide wire 115, pull strings 120 etc.

Figure 1B:
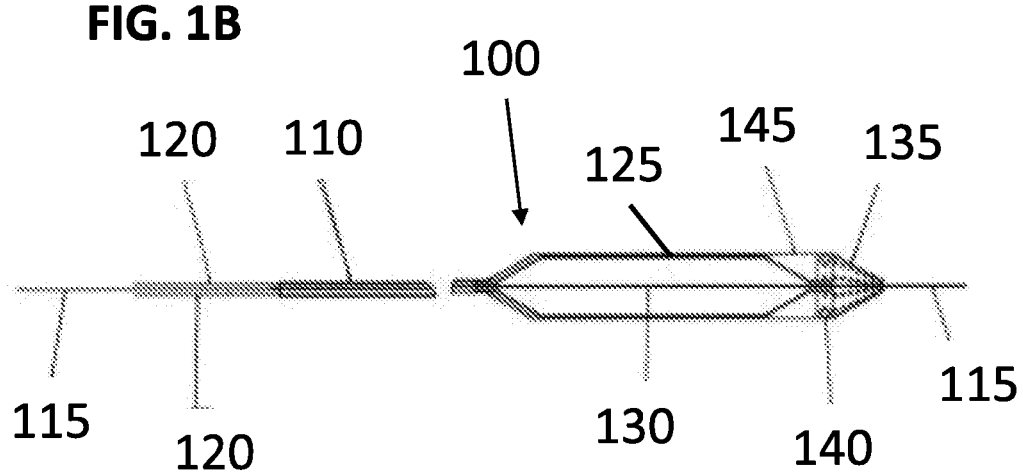
FIG. 1B is a schematic diagram of a clot removal device with distal filter, deployed position while it is mounted on a guide wire according to some embodiments.
Figure 1C:
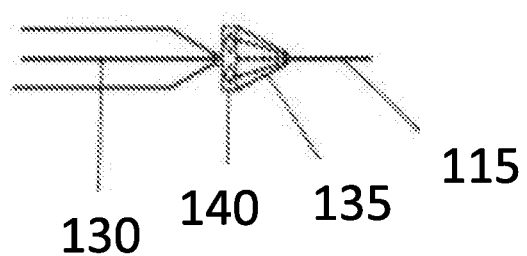
FIG. 1C is a schematic diagram of a clot removal device with distal filter, deployed position while it is mounted on a guide wire according to some embodiments.
Figure 1D:
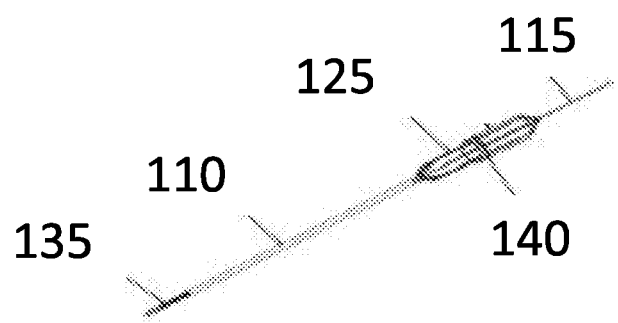
FIG. 1D is a schematic diagram of a clot removal device with distal filter, deployed position while it is mounted on a guide wire according to some embodiments.

As can be seen in FIGS. 1B and 1C, clot removal device 100 in expanded mode may include clot catcher 125, including distal filter mesh 135, supporting radial element 140, pulling wire 145, and clot holding element 130. In general, by pulling catheter 110 backward, clot holding element 130 and/or guide wire 115 is expanded radially, to penetrate a target clot, and trap or lock onto the clot.

Figure 1E:
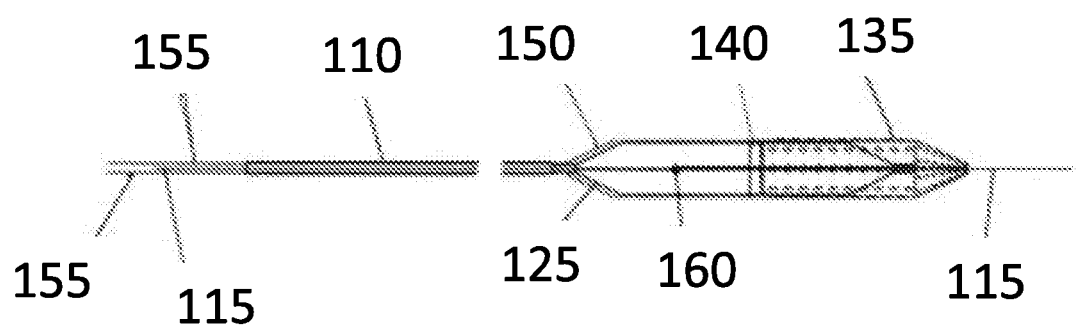
FIG. 1E is a schematic diagram of a clot removal device with distal filter, deployed position while it is mounted on a guide wire according to some embodiments.
Figure 1F:
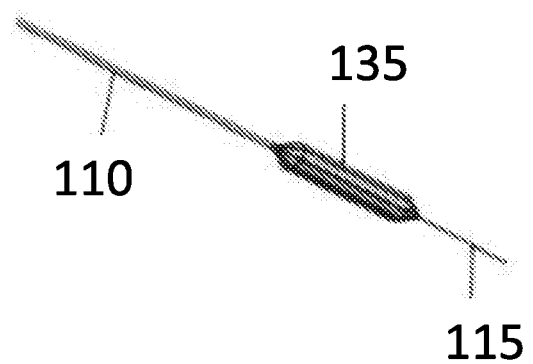
FIG. 1F is a schematic diagram of a clot removal device with distal filter, deployed position while it is mounted on a guide wire according to some embodiments.
Figure 1G:
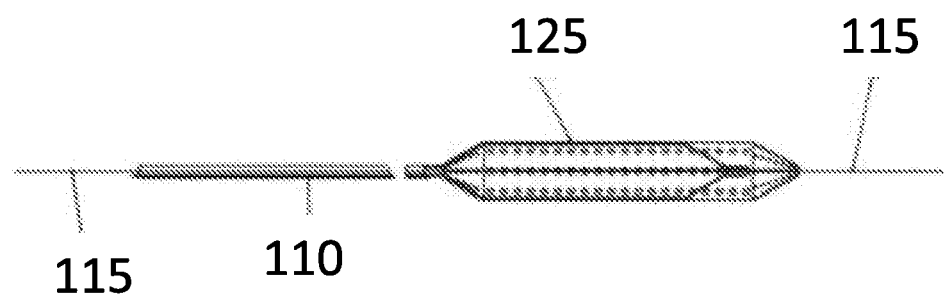
FIG. 1G is a schematic diagram of a clot removal device with distal filter, deployed position while it is mounted on a guide wire according to some embodiments.
Figure 2A:
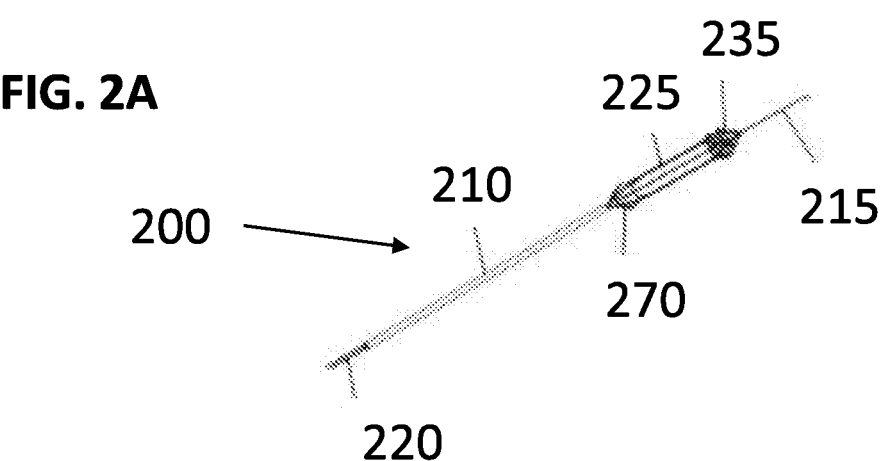
FIG. 2A is a schematic diagram of a clot removal device with distal and proximal filter, and showing a deployed proximal filter, while it is mounted on a guide wire, according to some embodiments.
Figure 2B:
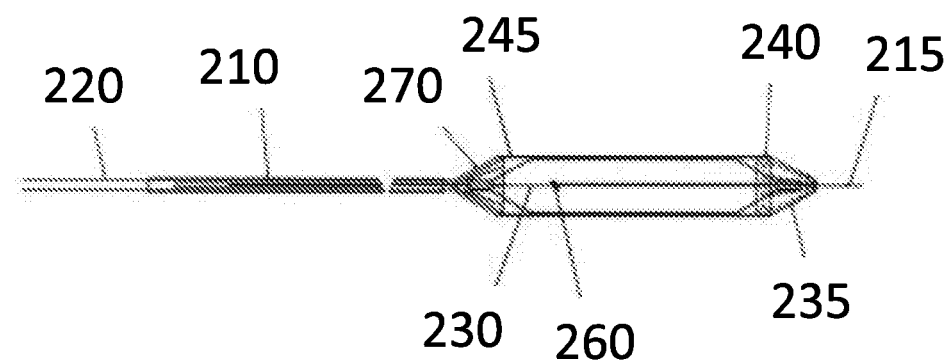
FIG. 2B is a schematic diagram of a clot removal device with distal and proximal filter, deployed position while it is mounted on a guide wire according to some embodiments.
Figure 2C:
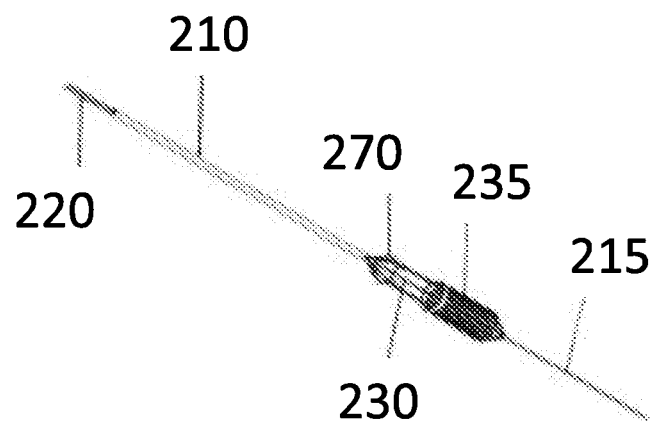
FIG. 2C is a schematic diagram of a clot removal device with distal and proximal filter, deployed position while it is mounted on a guide wire according to some embodiments.
Figure 2D:
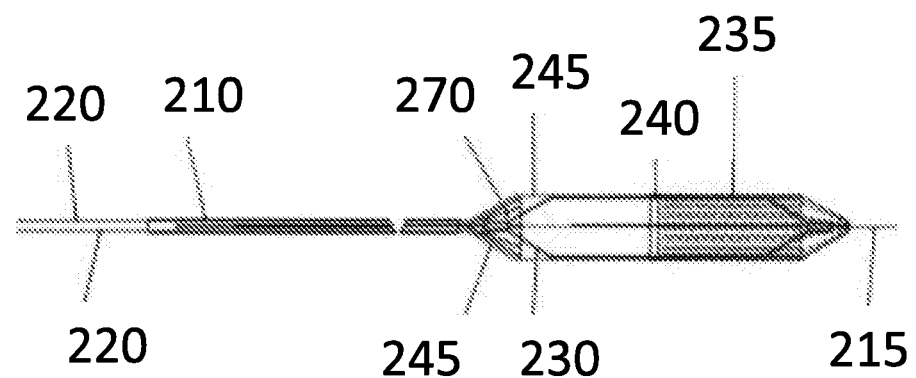
FIG. 2D is a schematic diagram of a clot removal device with distal and proximal filter, deployed position while it is mounted on a guide wire according to some embodiments.
Figure 2E:
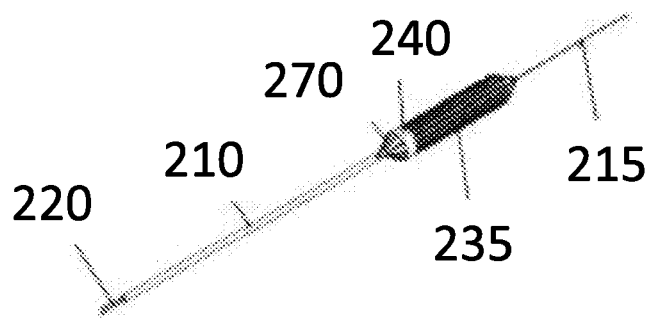
FIG. 2E is a schematic diagram of a clot removal device with distal and proximal filter, deployed position while it is mounted on a guide wire according to some embodiments.
Figure 2F:
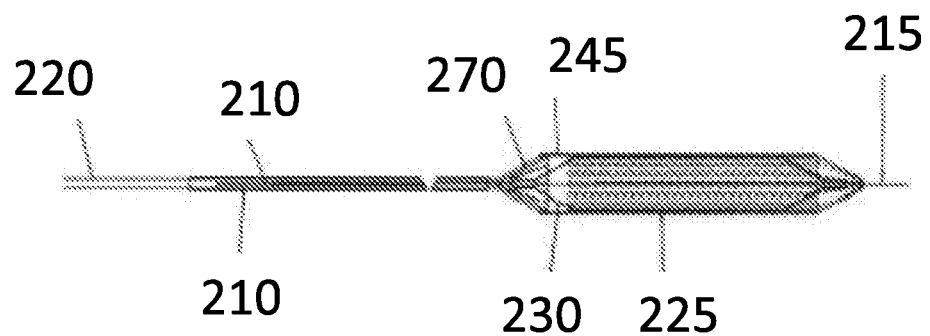
FIG. 2F is a schematic diagram of a clot removal device with distal and proximal filter, deployed position while it is mounted on a guide wire according to some embodiments.
Figure 3A:
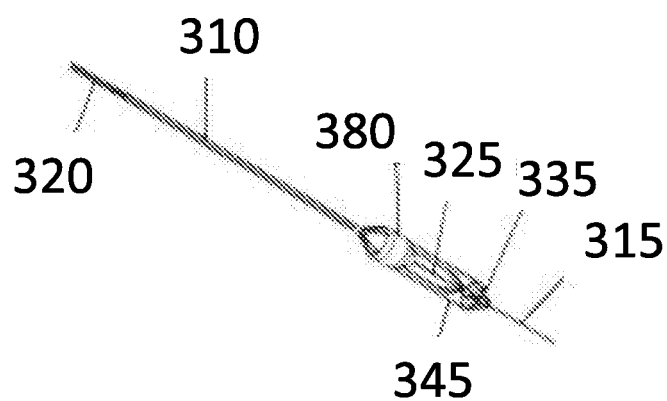
FIG. 3A is a schematic diagram of a clot removal device with distal filter and a proximal balloon, and showing a deployed distal filter and a proximal balloon, according to some embodiments.
Figure 3B:
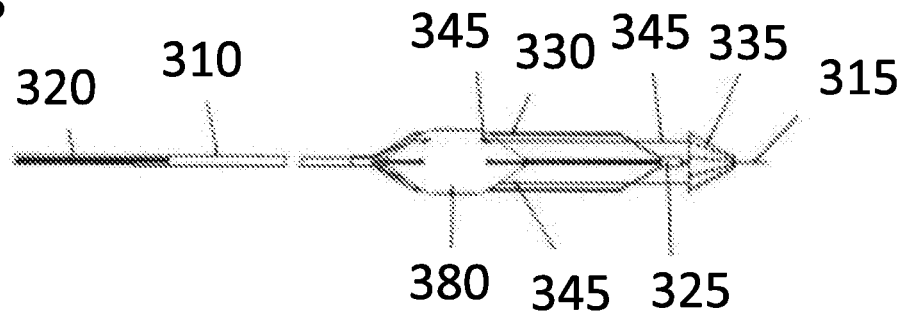
FIG. 3B is a schematic diagram of a clot removal device with distal filter and proximal balloon, in deployed position while it is mounted on a guide wire according to some embodiments.
Figure 3C:
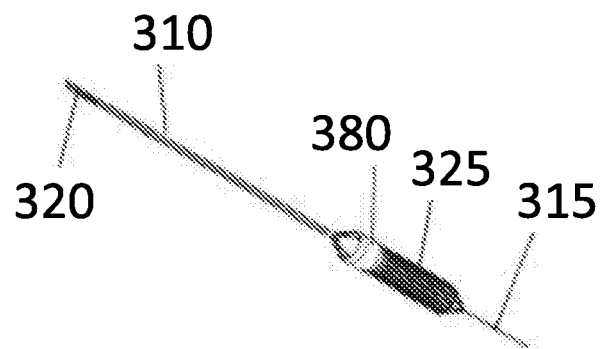
FIG. 3C is a schematic diagram of a clot removal device with distal filter and proximal balloon, in deployed position while it is mounted on a guide wire according to some embodiments.
Figure 3D:
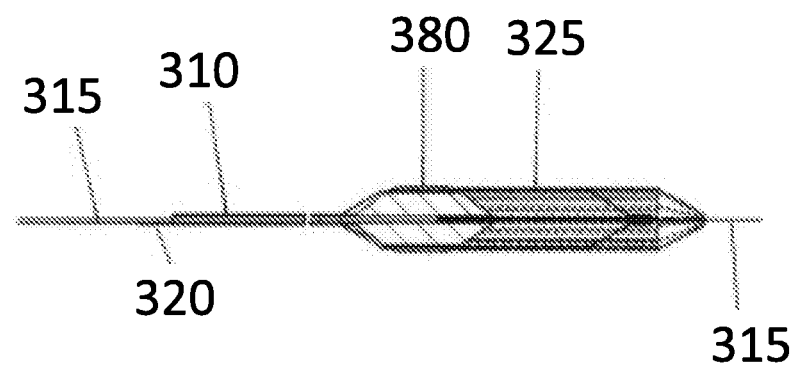
FIG. 3D is a schematic diagram of a clot removal device with distal filter and proximal balloon, in deployed position while it is mounted on a guide wire according to some embodiments.
Figure 3E:
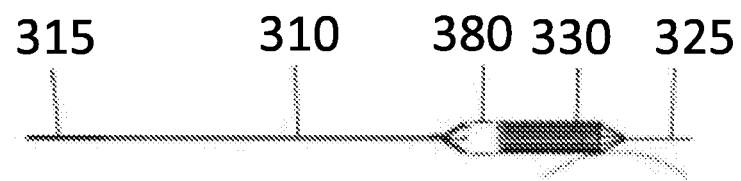
FIG. 3E is a schematic diagram of a clot removal device with distal filter and proximal balloon, in deployed position while it is mounted on a guide wire according to some embodiments.

As can be seen in FIGS. 1D-1G, clot catcher 125 may be subsequently advanced into a position for deployment of distal filter 135 (may be advanced slowly or spontaneously), optionally still within the guidewire, through the target clot, to a position beyond the target clot. When in position, pull string(s) 120 may be pulled, thereby deploying distal filter mesh 135 downstream to the target clot, to form a pocket type structure to capture the clot. As seen in FIG. 1E, by pulling the mesh proximally the mesh may be exposed to form a clot holding pocket, optionally at deployment position 160. As seen in FIG. 1F, the deployment of the mesh may be seen around half way to its target, still in a folded-up position.

FIGS. 2A-2F are schematic diagrams of a clot removal device with a double clot capture filter, and showing a deployed proximal filter, while it is mounted on a guide wire, according to some embodiments. As can be seen, clot removal device 200 may be mounted on a guide wire 215. Clot removal device 200 may be initially crimped in a guiding catheter 210. Upon deployment of clot removal device 200 into a target artery, positioned adjacent to a target clot, one or more elements may be deployed outside guiding catheter 210. Clot removal device 200 may include a distal filter mesh 235 and a proximal filter mesh 270.

As can be seen, proximal filter 270 may be deployed to enable substantially full capture of a target clot, thereby securing the clot from dislodging from the proximal edge of distal filter 235. Once proximal filter 270 engages around a target clot in unison with distal filter 215, the clot is secured and can be retrieved safely. In addition, filter 270 can be positioned distally to distal filter 235, or vice-versa. In all cases, while pushing catheter 210 distally, proximal filter 270 secures distal filter 235 from opening during retrieval in narrows areas, such as lesions.

FIGS. 3A-3E are schematic diagrams of a clot removal device with a distal filter and a proximal balloon, according to some embodiments. As can be seen, clot removal device 300 may be mounted on a guide wire 315. Clot removal device 300 may be initially crimped in a guiding catheter 310. Upon deployment of clot removal device 300 into a target artery, positioned adjacent to a target clot, one or more elements may be deployed outside guiding catheter 310. Clot removal device 300 may include a distal filter mesh 335 and a proximal filter balloon 380.

As can be seen distal filter 335 and a proximal balloon 380 act as a guide for clot holder 330, filter 335, and various wires or controllers, such as 345, 325 and 315. When the removal device is positioned prior to a target clot in a treatment vessel, clot grabbing or stabilizing element 325 is expanded to penetrate the target clot, and to grab the clot. Balloon 380 is then expanded proximally to the clot, to act as a support to prevent the clot removal device and/or clot form moving downstream in the vessel. The distal filter may subsequently be grabbed back in the vessel, taking the clot with it, into balloon 380, and the balloon may then be deflated, in order to keep the clot sealed in the balloon, for extraction or retrieval from the body, via catheter 310.

In further embodiments, distal filter 315 may be unfolded with a pusher mechanism that operates mechanically or manually from a proximal handle.

In additional embodiments, clot holder 325 may have a radial force control mechanism that may opened by a pusher or puller, operated mechanically or manually from a proximal handle.

Figure 4:
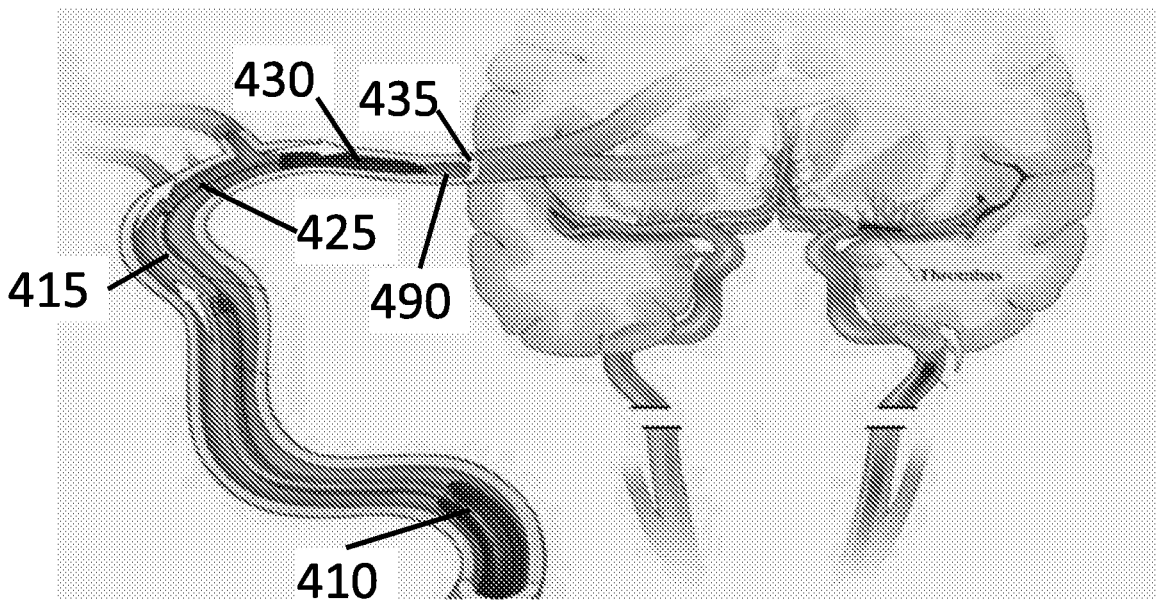
FIG. 4 is a graphical illustration of an example of a clot removal device with a distal filter, in the process of being according to some embodiments.

FIG. 4 is a graphical illustration of an example of a clot removal device with a distal filter 435, showed in an example of deployment around a clot 490 in the brain, according to some embodiments.

Figure 5:
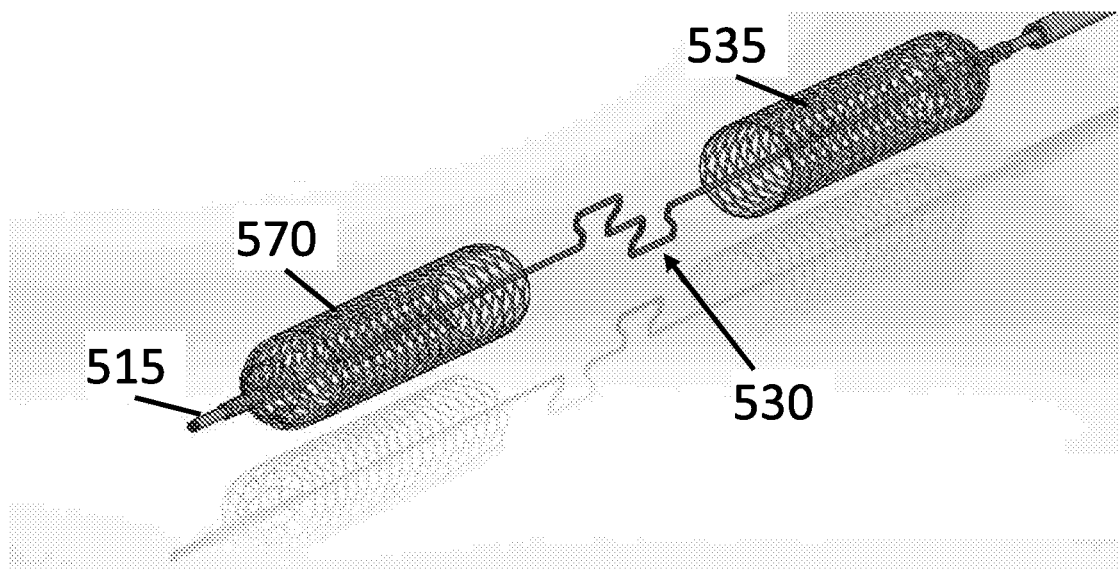
FIG. 5 is a graphical illustration of an example of an expanded clot removal device with a proximal and distal filter, according to some embodiments.

FIG. 5 is a graphical illustration of an example of an expanded clot removal device with a proximal and distal filters, according to some embodiments. As can be seen proximal filter mesh 535 and distal filter mesh 570 may be expanded around a target clot, and clot or plaque grabbing, trapping and/or stabilizing element 530, may be expanded inside the target clot, to grab, hold or stabilize the clot, until ready to be retrieved. In some examples, clot grabbing element 530 may be a Nitinol wire, pre-shaped to expand into a clot. For example, a 0.25 mm Nitinol wire may be used, or wires of other sizes or thicknesses. Of course, other wire or structure types may be used, using other materials, and in other sizes or profiles.

In further embodiments, one or more of filter meshes 535 and 570 may be designed with a mesh structure that has mesh structures of approximately 20-30 micron thickness, or in other cases between 10-50 micron thickness. Of course, other thicknesses may be used. Further, the mesh structure(s) may be designed with a greater density in the middle section (e.g., apertures, holes, windows, openings or gaps of between 0-100 microns) and a lesser density on the sides (e.g., holes of between 100-300 microns in diameter), to enable efficient grabbing of the clot and/or clot parts, since larger elements generally migrate on the sides of the vessels, whereas smaller elements generally migrate in the central areas of the vessel. In additional embodiments, the mesh aperture size may be between 50-500 microns in diameter across the length of the filter. In other cases, the mesh aperture may change size across the length of the filter.

Of course, other hole or gap sizes may be used. In this way, the outer area of the mesh, having larger gaps or holes, may allow for enhanced blood flow during the duration of a procedure, and still assure a high level of safety in terms of prevention downstream flow of clots or clot particles.

According to some embodiments, mesh holes may be designed to be rounded, square, or in other shapes optimized to form a mesh volume adapted to trap clots and/or clot elements.

According to some embodiments, meshes may be constructed using knitting, weaving, braiding, laser cutting or other techniques to enable suitable expandable meshes to be delivered.

In accordance with further embodiments of the present invention, the mesh filter(s) may be constructed from, but not limited to, a polymeric (e.g. PET, PE, PP, PTFE, EPTFE, etc.) or metal (e.g. steel, Nitinol, memory material etc.). Further, the mesh filter(s) may be constructed using braiding, weaving, knitting, laser drilling holes' etc. In some embodiments, the mesh filter(s) are designed to be flexible, able to accommodate turns and changing vessel radiuses.

According to some embodiments, the meshes may be coated with Anticoagulant compounds, for example, drugs or pharmaceuticals that act to prevent blood coagulation, and/or which prolong the clotting time.

According to some embodiments, the meshes may be coated with a medication or treatment compound.

As described above, mesh filters are adapted to collect substantially all downstream thrombus, plaque or clot fragments or elements during a clot or plaque removal procedure. Further, mesh filters are adapted to collect substantially all thrombus, plaque or clot fragments or elements during retrieval of a target clot or plaque to be removed. In still further embodiments, the distal and/or primal filter(s) described herein may have a controlled opening, optionally to cover a large thrombus and/or small thrombus elements. In still further usage of the clot removal device descried above, usage of the filter(s) described herein are useful reducing procedure time, for example, by facilitating clot or plague removal in a single procedure.

Figure 6A:
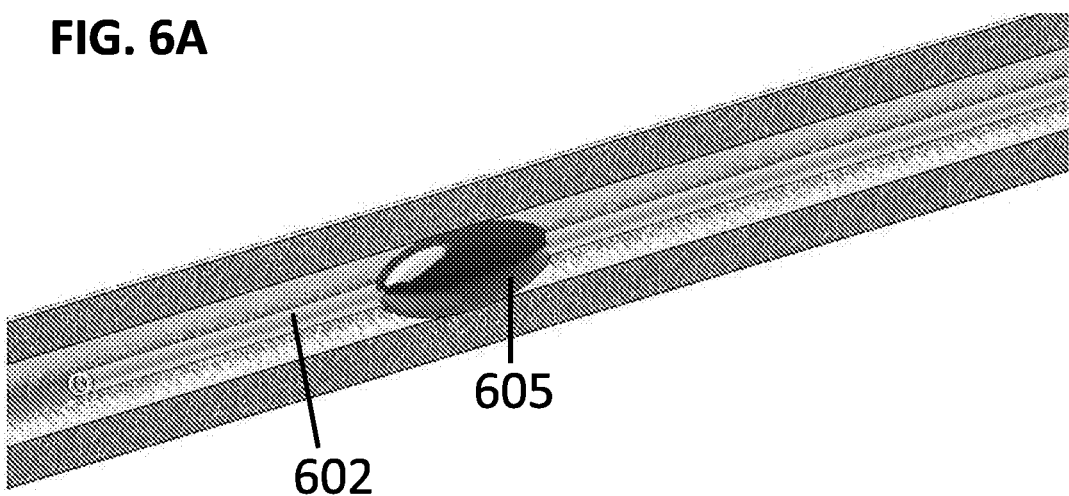
FIG. 6A is a graphical illustration of a first step in a clot removal procedure, using a clot removal device as described herein, according to some embodiments.
Figure 6B:
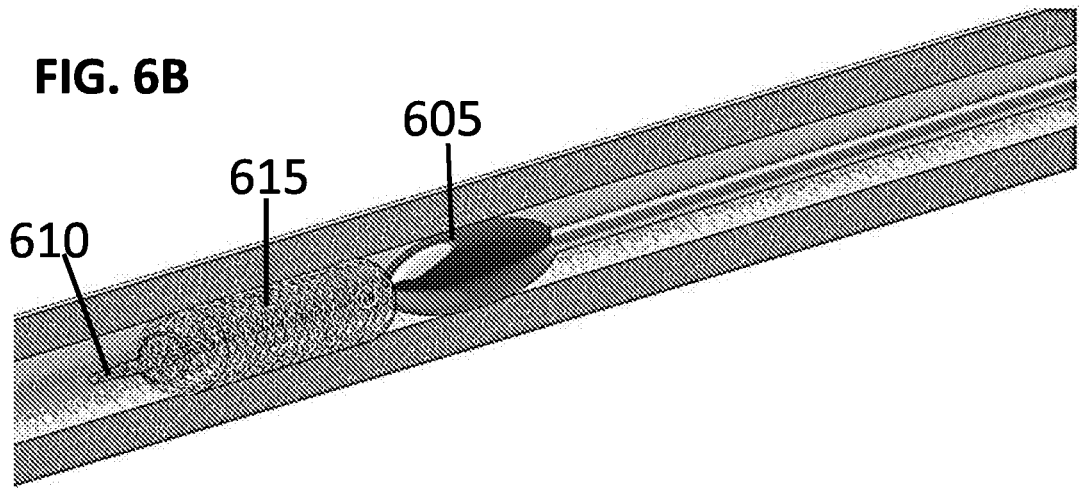
FIG. 6B is a graphical illustration of a second step in a clot removal procedure, using a clot removal device as described herein, according to some embodiments.
Figure 6C:
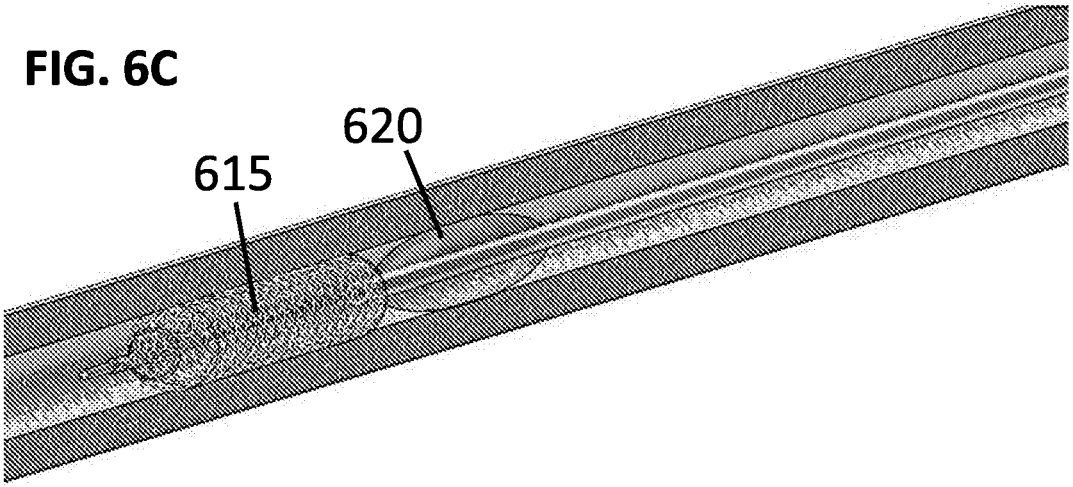
FIG. 6C is a graphical illustration of a third step in a clot removal procedure, using a clot removal device as described herein, according to some embodiments.
Figure 6D:
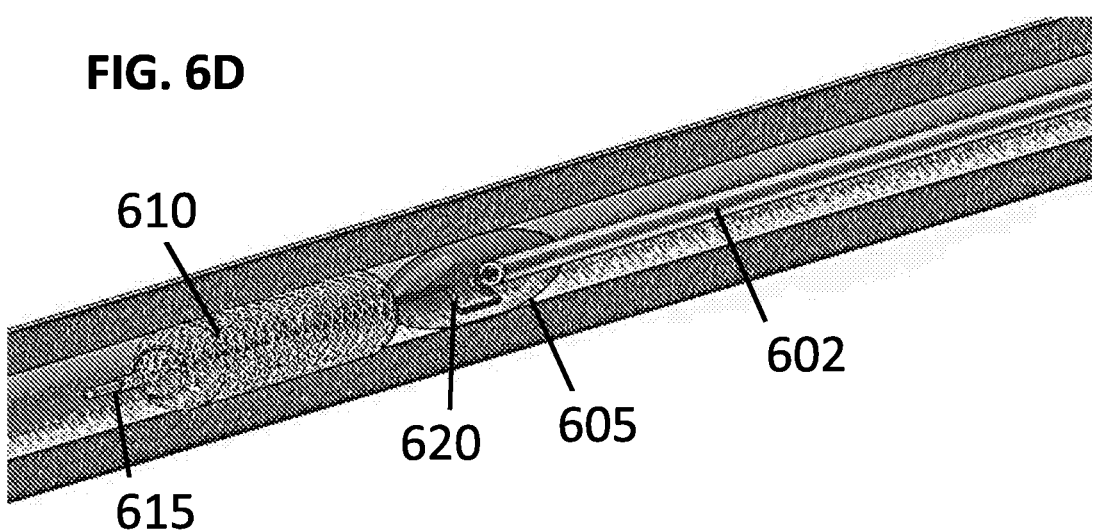
FIG. 6D is a graphical illustration of a forth step in a clot removal procedure, using a clot removal device as described herein, according to some embodiments.
Figure 6E:
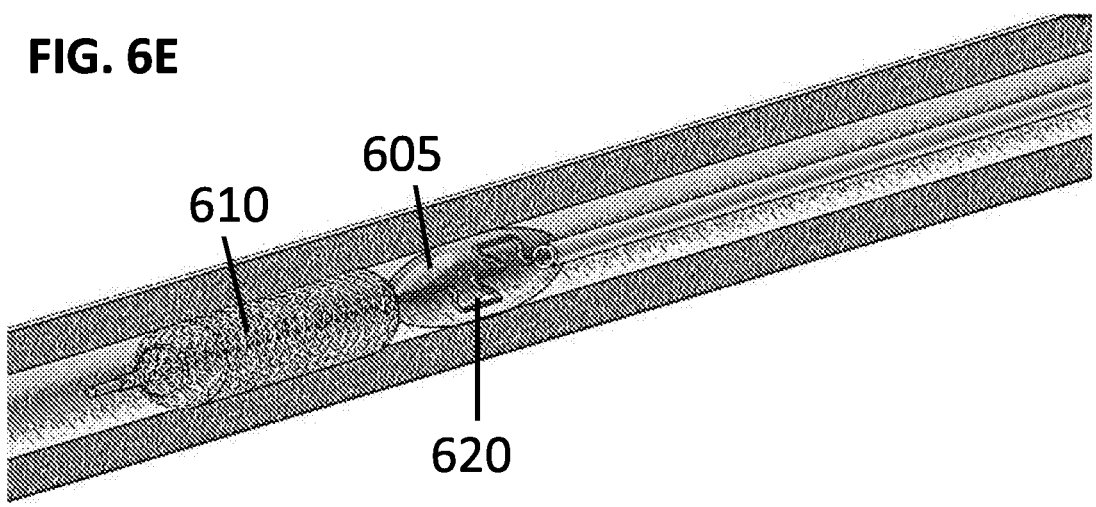
FIG. 6E is a graphical illustration of a fifth step in a clot removal procedure, using a clot removal device as described herein, according to some embodiments.
Figure 6F:
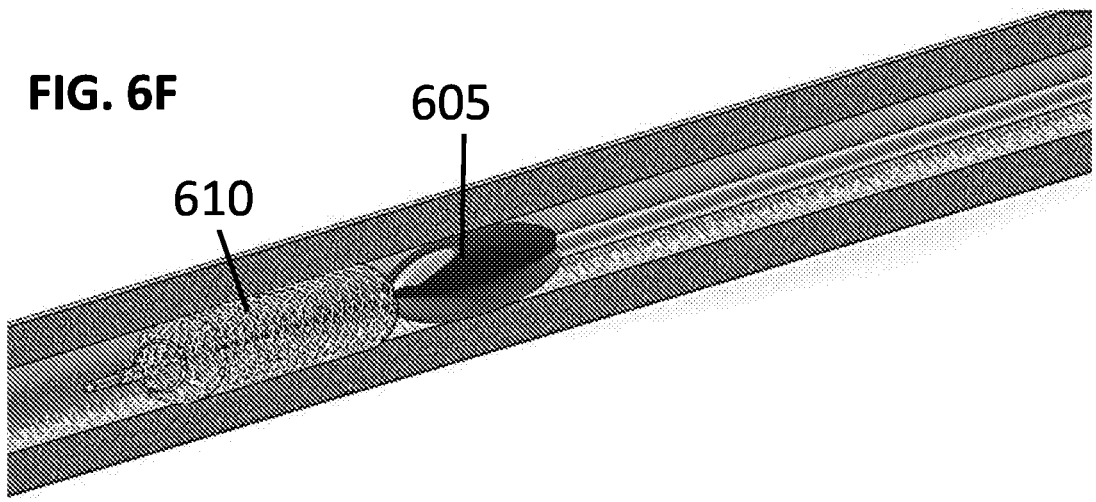
FIG. 6F is a graphical illustration of a sixth step in a clot removal procedure, using a clot removal device as described herein, according to some embodiments.
Figure 6G:
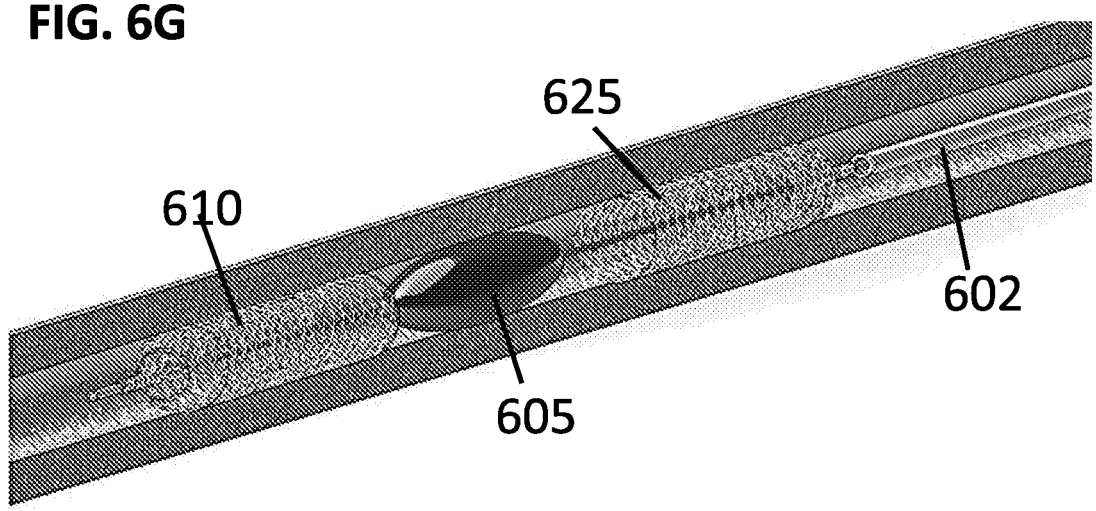
FIG. 6G is a graphical illustration of a seventh step in a clot removal procedure, using a clot removal device as described herein, according to some embodiments.
Figure 6H:
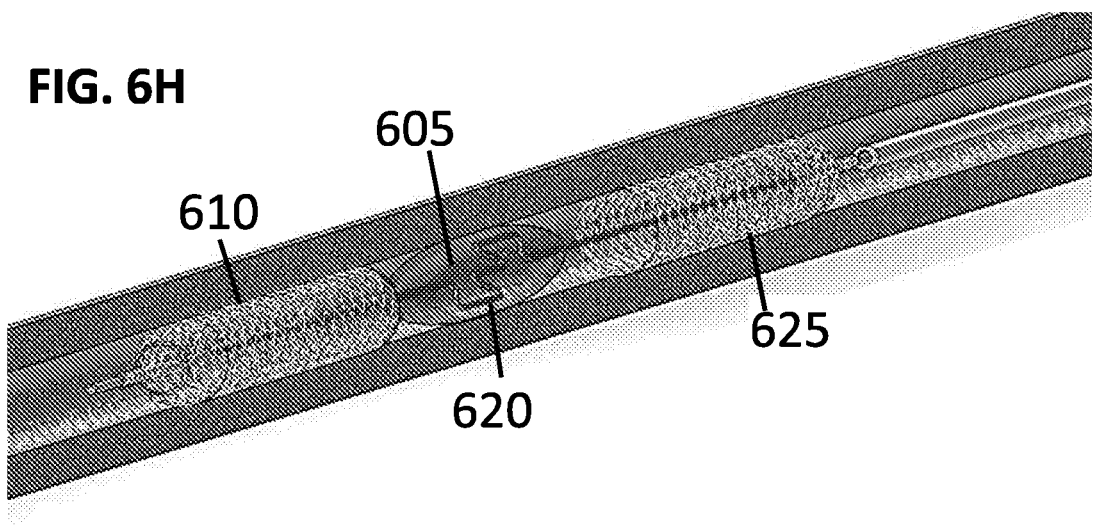
FIG. 6H is a graphical illustration of an eighth step in a clot removal procedure, using a clot removal device as described herein, according to some embodiments.
Figure 6I:
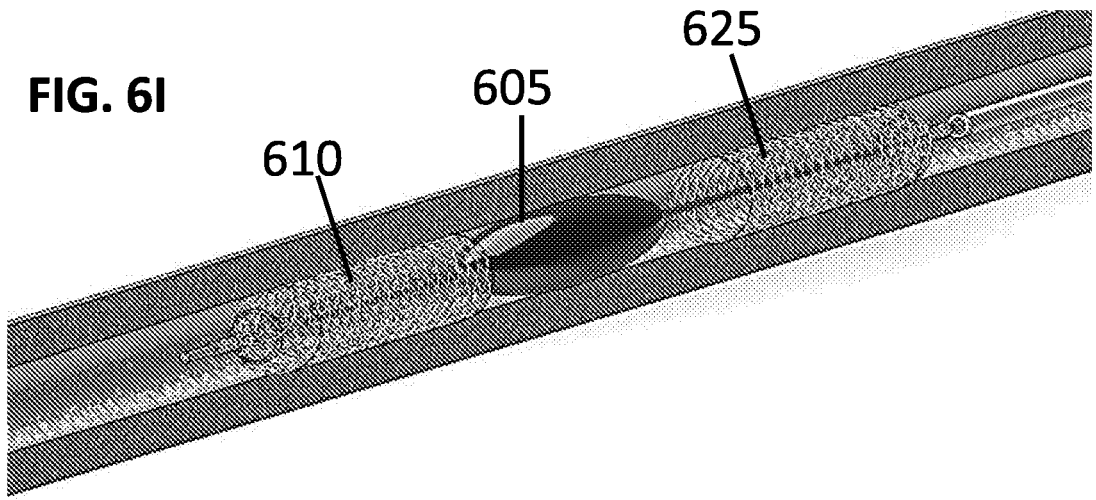
FIG. 6I is a graphical illustration of a ninth step in a clot removal procedure, using a clot removal device as described herein, according to some embodiments.
Figure 6J:
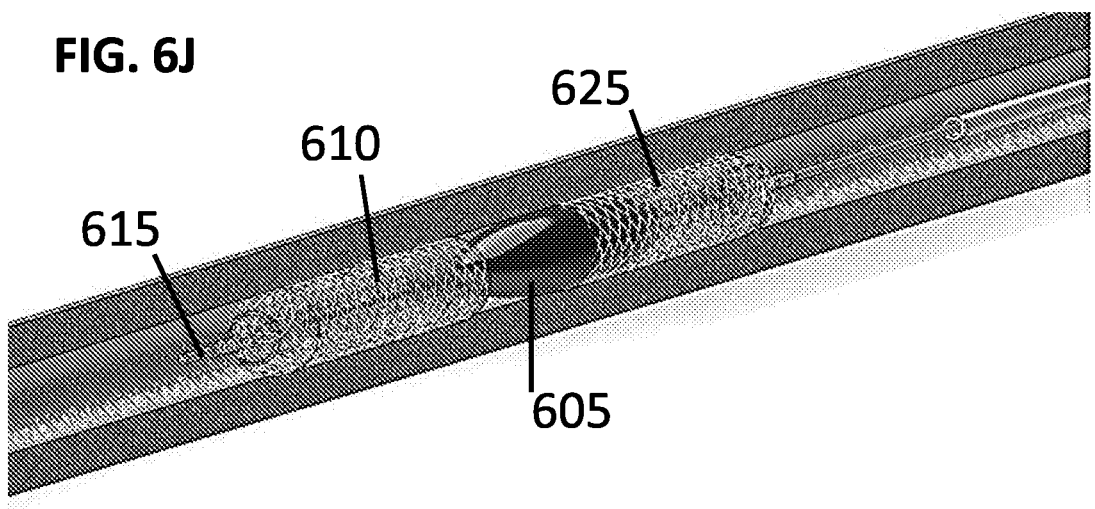
FIG. 6J is a graphical illustration of a tenth step in a clot removal procedure, using a clot removal device as described herein, according to some embodiments.
Figure 6K:
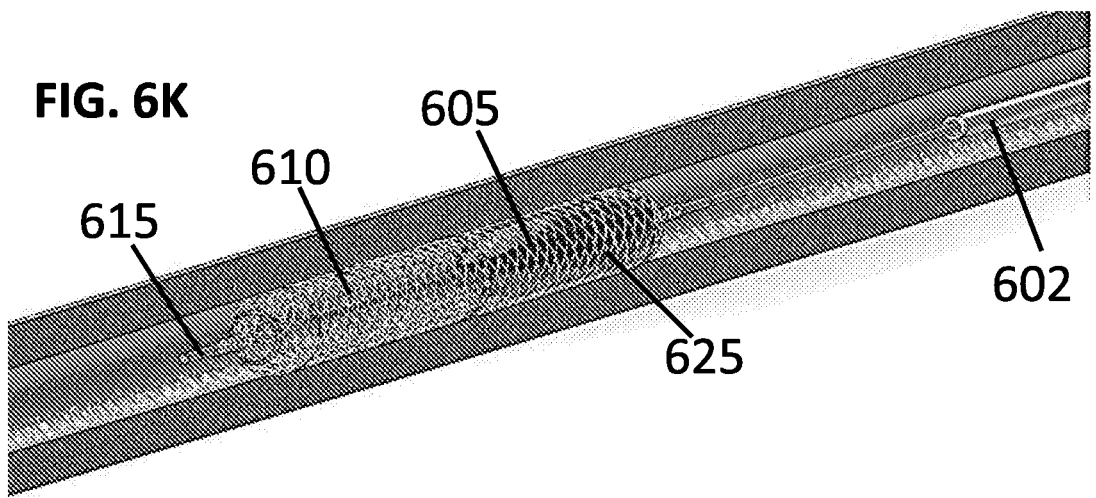
FIG. 6K is a graphical illustration of an eleventh step in a clot removal procedure, using a clot removal device as described herein, according to some embodiments.
Figure 6L:
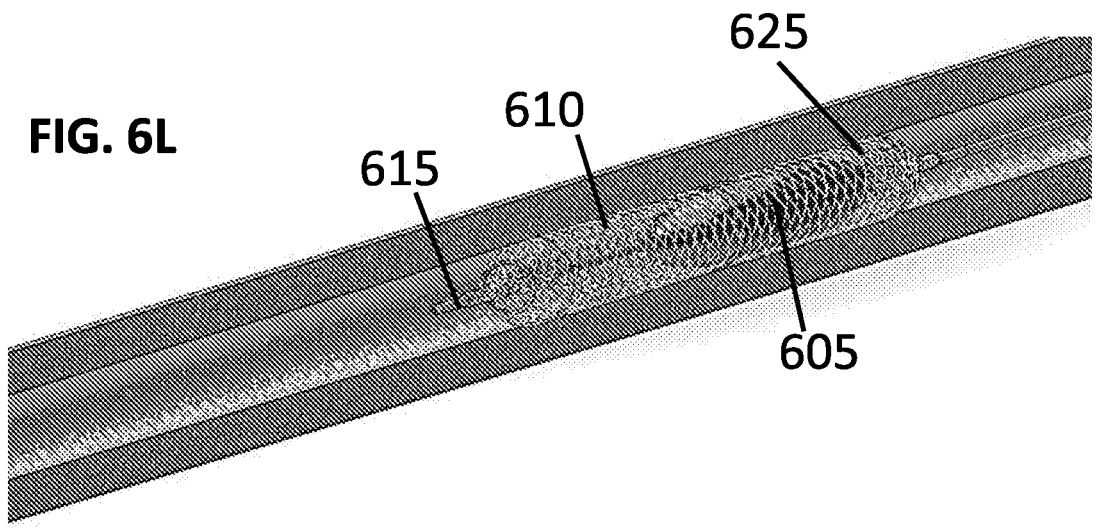
FIG. 6L is a graphical illustration of a twelfth step in a clot removal procedure, using a clot removal device as described herein, according to some embodiments.

FIGS. 6A-6L are a series of animations illustrating a deployment and treatment procedure using the clot removal device as described in FIGS. 1-5, according to some embodiments. As can be seen, in FIG. 6A, after positioning the clot retrieval device proximal to a target clot 605, a device catheter 602 with a guide wire penetrates the clot and transcends the clot. In FIGS. 6B and 6C, device catheter is withdrawn to reveal guide wire 610, and further, distal filter mesh 615 is expanded or deployed beyond the clot, which acts to substantially prevent the clot or clot particles from flowing downstream. In FIGS. 6D-6F, as catheter 602 is further withdrawn, clot grabbing, stabilizing or holding element 620 is revealed. Further, grabbing element 620 expands as per a pre-configured design, to help grab or grip target clot 605. In FIGS. 6G-6I, further withdrawal of catheter 602, or usage of another controller, enables expansion of a proximal filter mesh 625, proximal to target clot 605. In FIG. 6J, extraction of guide wire 615 or other controller element(s) allows distal mesh 610 to be partially withdrawn, thereby grabbing clot 605 into the receiving proximal mesh 625. In FIGS. 6K and 6L, further extraction of guide wire 615 or other controller element(s) allows distal mesh 610 to be further withdrawn, thereby pushing clot 605 fully into the receiving proximal mesh 625. Clot 605 is hereby trapped in the chamber formed by meshes 610 and 625, and may now be retrieved from the target, via catheter 602 or other controllers.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. A clot removal device, comprising:
a guide wire and one or more control wires;
an expandable clot holding element configured for penetrating and expanding inside a target clot and stabilizing the target clot in its position inside a treatment vessel;
a controllable distal filter mesh mounted on said guide wire and configured for deployment downstream from the target clot, said controllable distal filter mesh configured to substantially prevent downstream migration of clot elements and for controllable expansion and/or retraction thereof by said one or more control wires for retrieval of the stabilized target clot by the clot removal device;
a proximal filter mesh, openable upstream from the stabilized target clot and configured to secure the target clot stabilized by the expandable clot holding element in a clot holding area defined between said controllable distal and proximal filter meshes during the retrieval by the clot removal device.

2. The device of claim 1, wherein at least one of the proximal and the controllable distal filter meshes are wire configurations designed with a mesh structure having a thickness of about 20-30 microns.

3. The device of claim 2, wherein the controllable distal filter mesh and the proximal filter mesh are designed to connect to each other to secure the target clot stabilized by the expandable colt holding element within the clot removal device.

4. The device of claim 1, further comprising a proximal balloon, designed to encapsulate the target clot prior to retrieval by the clot removal device.

5. The device of claim 1, wherein the clot holding element includes a memory material frame designed to expand inside the clot to stabilize the clot in its current position.

6. The device of claim 1, wherein the distal filter mesh has gap sizes of a plurality of sizes, to enable substantial prevention of clot portion escape while enabling substantial blood flow during a clot removal procedure.

7. The device of claim 1, wherein the distal filter mesh is designed to be mechanically or manually unfolded by the one or more control wires, when in a position downstream from the target clot.

8. The device of claim 1, further comprising a treatment catheter designed to maintain elements of the clot removal device crimped inside the catheter during insertion into a vessel, and enabling controlled expansion and/or contraction of one or more clot removal device elements during a clot removal procedure.

9. The device of claim 1, wherein the distal filter mesh and/or the proximal filter mesh are coated with an anticoagulant compound.

10. The device of claim 1, wherein the distal filter mesh and/or the proximal filter mesh are coated with a medication or treatment compound.

11. The device of claim 1, wherein the distal filter mesh and/or the proximal filter mesh are ogive shaped.

12. The device of claim 1, wherein the clot holding element is expandable to a non-linear shape to provide increased surface area to hold the target clot.

13. The device of claim 1, being configured so that the distal filter mesh and the proximal filter mesh can be drawn toward each other to close around the target clot.

14. A method of removing a clot from a vessel, comprising:
advancing a treatment catheter carrying a clot removal device in a vessel towards a target clot to be removed;
advancing the clot removal device to a position proximal to the target clot;

extending a guide wire through the target clot;
expanding a distal mesh at a distal side of the clot;
expanding a clot stabilizing wire inside the clot for stabilizing the clot in its position inside the vessel;
expanding a proximal mesh on a proximal side of the clot; and
withdrawing the distal mesh with the clot stabilized on the stabilizing wire towards the proximal mesh, thereby securing the clot in a clot holding area defined between said controllable distal and proximal filter meshes, for retrieval from the vessel through the treatment catheter.

15. The method of claim 14, further comprising expanding a proximal balloon on a proximal side of the clot; and
withdrawing the distal mesh with the stabilized clot towards the proximal balloon, thereby securing the clot in a clot holding area, during retrieval from the vessel.

16. The method of claim 14, further comprising applying one or more anticoagulant compounds to one or more elements of the clot removal device.

17. The method of claim 14, further comprising applying one or more medication compounds to one or more elements of the clot removal device.

\* \* \* \* \*